(12) United States Patent
Hwang

(10) Patent No.: US 6,652,816 B2
(45) Date of Patent: Nov. 25, 2003

(54) APPARATUS FOR GENERATING OZONE AND ANION

(76) Inventor: Hyeon-Bae Hwang, 306-1004, Mirabo 3th A.P.T., 19/6 229, Unam 3-dong, Buk-Gu, Kwangju-city (KR)

( * ) Notice: Subject to any disclaimer, the term of this patent is extended or adjusted under 35 U.S.C. 154(b) by 173 days.

(21) Appl. No.: 09/956,072

(22) Filed: Sep. 20, 2001

(65) Prior Publication Data

US 2002/0076369 A1 Jun. 20, 2002

(30) Foreign Application Priority Data

Sep. 23, 2000 (KR) ................................ P2000/56040
Dec. 13, 2000 (KR) ................................ P2000/75914
Apr. 9, 2001 (KR) ................................ P2001/009781
Jul. 27, 2001 (KR) ................................ P2001/045312

(51) Int. Cl.[7] ............................................... B01J 19/08
(52) U.S. Cl. ........................... 422/186.07; 422/186.12; 422/186.04; 422/121
(58) Field of Search .................. 422/186.04, 186.07, 422/186.12, 121

(56) References Cited

U.S. PATENT DOCUMENTS 5,656,063 A * 8/1997 Hsu ............................. 96/58
6,447,731 B1 * 9/2002 Sun et al. ............... 422/186.07

* cited by examiner

Primary Examiner—Krishor Mayekar
(74) Attorney, Agent, or Firm—Burns, Doane, Swecker & Mathis, L.L.P.

(57) ABSTRACT

An apparatus for generating ozone and anion capable of respectively controlling an ozone generator and an anion generator is disclosed. The apparatus includes an ozone generator, an ozone generator-driving portion, a second power source supplying power to the ozone generator-driving portion, an anion generator, an anion generator-driving portion, a circulating fan circulating the generated anion, a first power source supplying power to the anion generator-driving portion, a selecting valve selectively discharging the anion generated from the anion generator to a water purifier 100 or an ozone container, an activated carbon filter removing smell of the ozone introduce through the selecting valve into the water purifier, a controlling portion controlling the anion generator-driving portion and the ozone generator-driving portion, an operating portion inputting an external instruction to the controlling portion, and a timer controlling a reserving function of the operating portion.

8 Claims, 7 Drawing Sheets

FG.9

APPARATUS FOR GENERATING OZONE AND ANION

This application claims priority under 35 U.S.C. §§119 and/or 365 to 1) P2000/56040, 2) P2000/75914, 3) U2001/009781 and 4) P2001/045312 filed in Republic of Korea on 1) Sep. 23, 2000, 2) Dec. 13, 2000, 3) Apr. 9, 2001 and 4) Jul. 27, 2001; the entire content of which is hereby incorporated by reference.

BACKGROUND OF THE INVENTION

1. Field of the Invention

The present invention relates to an apparatus for generating ozone and anion and, more particularly, to an apparatus for generating ozone and anion, which is capable of respectively controlling an ozone generator and an anion generator according to a using purpose and also conveniently controlling various functions.

2. Description of the Related Art

Ozone is colorless and odorous gas having strong oxidizing power and comprising a molecule of three oxygen atoms. The ozone has a boiling temperature of 115° C. and a dissolving temperature of 192.5° C. The gas is 1.5 times as heavy as air. Therefore, if the ozone is leaked, the ozone is collected at a lower portion than the air.

The ozone has been stably used in various fields, e.g., a large-scaled water purification plant, in Europe and America over one hundred years ago. Further, in a natural state, the ozone forms an ozone layer in the stratosphere so as to protect human beings from intense ultraviolet rays generated from the sun.

The permissible level of ozone in working environment for a long time is 0.1 ppm. Typically, natural ozone of about 0.05 ppm is contained in the air of a beach, and about 0.03 ppm is contained in the fresh air of a forest. Generally, a man can smell the ozone of 0.01~0.03 ppm contained in the air. Therefore, the origin of a word "ozone"also means "smell" in Greek.

Further, the ozone tends to be intensely resolved during radiating of heat energy. To this end, if the ozone is in a desired useful concentration, the ozone has a characteristic of being intensely resolved even at a lower temperature of −120° C. However, in a lower concentration, a resolving speed of the ozone at a room temperature is greatly reduced.

Herein, one of the most important properties of the ozone is the strong oxidizing power. The ozone can oxidize many chemical compounds that do not react with oxygen. These properties can be applied through lots of substantial applications. Particularly, the oxidizing power is used in a treating process of water such as drinking water, general-purpose water, water for a swimming pool and wastewater, etc.

The ozone does not leave a harmful residual substance at all, which is different from chlorine, when being used as an oxidizing agent. The ozone also has strong germicidal power and thus removes a bacterium and a virus. Further, the ozone has strong bleaching power. Moreover, the ozone reacts with cigarette smoke, odorous gas and various harmful organic substances so as to make them harmless.

In using the ozone as a sterilizing and germicidal agent and an oxidizing agent, one of the important advantages is in that the ozone resolves only the oxygen but does not release other undesirable substances in the water. Substantially, the resolved oxygen is a very useful substance in the drinking water or the water for a swimming pool.

Therefore, the ozone has a sterilizing and germicidal property that does not exert any undesirably influence on external form, taste and smell of the water.

The ozone can be produced in various methods. For example, the ozone is generated by an electrical or chemical producing process, or by heating gaseous oxygen or exposing infrared rays in the air.

Substantially, in the producing process of the ozone, high-tension electricity is applied to the flow of oxygen (e.g., air), which contains the ozone gas. At this time, "Silent discharge" generated by the high-tension electricity transforms a part of the oxygen into the ozone, and also generates ultraviolet rays at the same time.

However, in the ozone generator, as described above, there are some problems that a discharging portion is rapidly corroded, thereby reducing a life span, and it is difficult to use it at home, since its volume is too large and its way of using is very complicate.

SUMMARY OF THE INVENTION

Therefore, it is an object of the present invention to provide an apparatus for generating ozone and anion, in which an ozone generator has a small volume and an anion generator is additionally provided, and the ozone generator and the anion generator can be respectively controlled, and the ozone and the anion are independently or simultaneously generated according to an using purpose so as to be supplied to an indoor space or to be dissolved in various kinds of raw water, thereby sterilizing the water and removing odor of the water and thus providing clean water.

To achieve one of the aforementioned objects of the present invention, there is provided an apparatus for generating ozone and anion so as to clean air and sterilize water for drinking and various vegetables/fruits, comprising an ozone generator 50 for generating ozone having a desired concentration, an ozone generator-driving portion 40 for driving the ozone generator, a second power source 45 for supplying power to the ozone generator-driving portion 40, an anion generator 35 for generating anion having a desired quantity of electric charge, an anion generator-driving portion 20 for driving the anion generator 35, a circulating fan 30 for facilely circulating the anion generated from the anion generator 35 to an outside, a first power source 25 for supplying power to the anion generator-driving portion 20, a selecting valve 60 for selectively discharging the anion generated from the anion generator 50 to the water purifier 100 or the ozone container 300, an activated carbon filter 55 for removing specific smell of the ozone introduce through the selecting valve 60 into the water purifier 100, a controlling portion 15 for controlling the entire portions including the anion generator-driving portion 20 and the ozone generator-driving portion 40, an operating portion 10 for inputting an external instruction to the controlling portion 15, and a timer 75 for controlling a reserving function of the operating portion 10.

Preferably, the ozone generator comprises a cylindrical dielectric body 520 which is formed of quartz or glass, an external electrode 540 which is formed of a spring type conductor apart from the dielectric body 520 at a distance, and an internal electrode 550 which is formed of the spring type conductor in the dielectric body 520. The anion generator comprises an acicular portion 240 having a plurality of sharp needles at a front face thereof, a fixing frame 250 for fixing the acicular portion 240, a discharging plate 230 having a plurality of discharging holes 231 corresponding to the needles of the acicular portion 240 so as to efficiently generate the anion, and a grill plate 220 for facilely discharging the anion, wherein the acicular portion 240 has a negative terminal 241, 241-1 that is connected with an anion-generating electrode (−), and the discharging holes 231 of the discharging plate 230 are disposed to be apart from the acicular portion 240 at a distance, and a power-supplying terminal is provided at both sides of the anion generator so that the anion generator can be assembled and disassembled without distinction of an upper and lower portion.

Preferably, the operating portion 10 comprises a vegetable/fruit button 7 which is provided to completely remove and sterilize residual agricultural chemicals, synthetic detergents and various germs on the vegetables and the fruits so as to maintain freshness when storing the vegetables and the fruits for a long time, and to sterilize and clean table services and kitchen utensils, an ozone button 6 which is provided to obtain a beauty effect but not used as water for drinking, a clean water button 1 which is provided to provide the water for drinking, which is completely harmless in an aseptic state, a clean air button 2 that generates the anion for sterilizing and purifying the air, and is performed for a predetermined time, or continuously performed, or performed in a sleep mode, a number displaying button 8 that is operated or controlled by the time and ozone increasing and decreasing buttons 4, 5 when displaying a time and when displaying the amount of ozone in the ppm unit; and a reserving button 9 that automatically generates the anion after completing a function of the vegetable/fruit button 7, the ozone button 6 and the clean water button 1, and that is interlocked with the timer 75 so as to reserve each function of the buttons.

Further, the ozone container comprises a main body 700 for receiving the ozone supplied through the ozone-supplying hose 210 from an external ozone generator, a cover 600 for removing residual ozone that is reacted with raw water in the main body 700, and a main unit 800 that efficiently supplies the ozone supplied from an outside and includes various devices for purifying the raw water so that a user can drink.

Moreover, the cover 600 comprises an ozone intake port 611 through which the residual ozone in the ozone container is sucked, an activated carbon 612 which is provided to remove the residual ozone, an outlet port 610 for discharging the residual ozone to an outside, and a locking pin 620 for sealingly coupling the cover 600 to the main body 700.

Preferably, the apparatus of claim 6, wherein the main unit 800 comprises a raw water intake 842 for sucking raw water from the main body 700, an underwater motor 841 for mixing the ozone supplied from an outside with the sucked raw water and then discharging the mixed raw water, an ozone discharging port 840 for discharging the mixed raw water, a former processing filter 831 for firstly processing the raw water processed by the ozone so as to remove contaminants, foreign substances, floating matters formed of solid substances and deposits of 5 $\mu$ or more, an activated carbon filter 833 for removing various chemical substances and contaminants, a purified water outlet port 810 for supplying the purified water through the activated filter 833 to the outside, a wastewater intake port 821 for receiving the wastewater, a filter 822 for filtering relatively large-sized substances such as various floating substances and deposits, and a wastewater outlet port 820 for discharging the wastewater to the outside.

BRIEF DESCRIPTION OF THE DRAWINGS

The above objects and other advantages of the present invention will become more apparent by describing in detail preferred embodiments thereof with reference to the attached drawings in which.

DETAILED DESCRIPTION OF THE PREFERRED EMBODIMENTS

Now, preferred embodiments of the present invention will be described in detail with reference to the annexed drawings.

Figure 1:
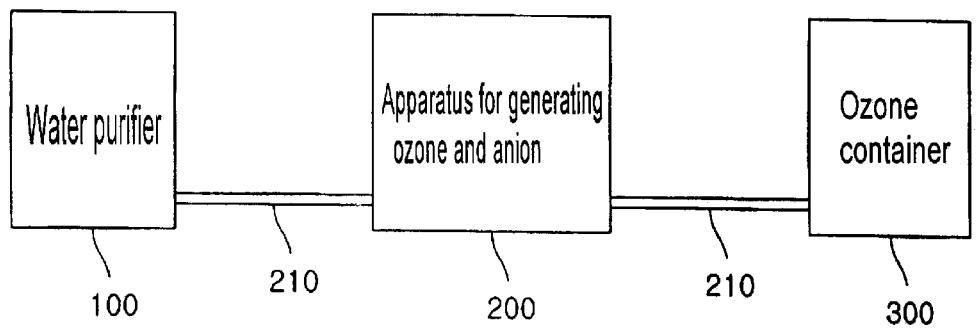
FIG. 1 is a block diagram showing a construction of an apparatus for generating ozone and anion, a water purifier and an ozone container according to the present invention.

FIG. 1 is a block diagram showing a construction of an apparatus for generating ozone and anion, a water purifier and an ozone container according to the present invention. As shown in FIG. 1, a water purifier 100 and an ozone container 300 are respectively connected through an ozone-supplying hose 210 formed of rubber to both sides of an apparatus 200 for generating ozone and anion according to the present invention.

Figure 2:
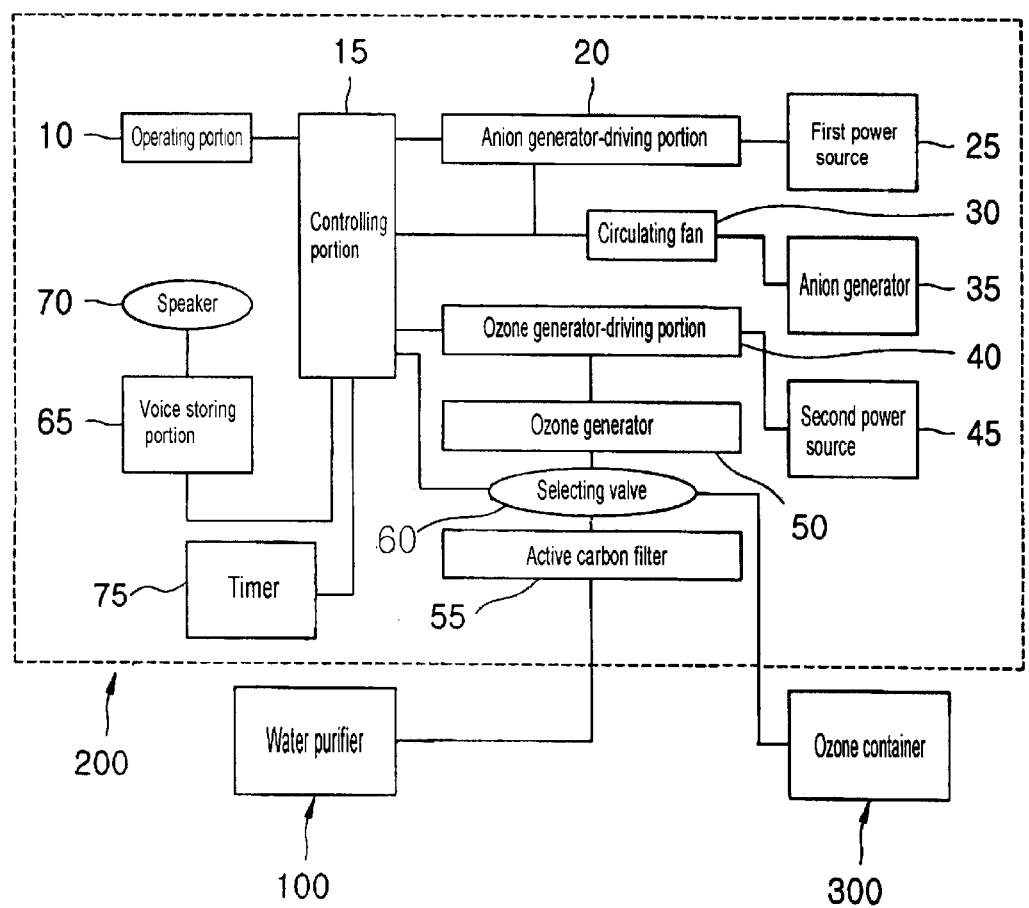
FIG. 2 is a block diagram of the apparatus for generating the ozone and anion according to the present invention.

As shown in FIG. 2, the apparatus 200 for generating ozone and anion comprises an ozone generator 50 for generating ozone having a desired concentration, an ozone generator-driving portion 40 for driving the ozone generator 50, a second power source 45 for supplying power to the ozone generator-driving portion 40, an anion generator 35 for generating anion having a desired quantity of electric charge, an anion generator-driving portion 20 for driving the anion generator 35, a circulating fan 30 for facilely circulating the anion generated from the anion generator 35 to an outside, a first power source 25 for supplying power to the anion generator-driving portion 20, a selecting valve 60 for selectively discharging the anion generated from the anion generator 50 to the water purifier 100 or the ozone container 300, an activated carbon filter 55 for removing specific smell of the ozone introduce through the selecting valve 60 into the water purifier 100, a controlling portion 15 for controlling the entire portions including the anion generator-driving portion 20 and the ozone generator-driving portion 40, an operating portion 10 for inputting an external instruction to the controlling portion 15, a timer 75 for controlling a reserving function of the operating portion 10, an voice storing portion 65 for informing an operation of the operating portion 10 and whether each portion is operated, with a voice, and a speaker for outputting the voice of the voice storing portion 65.

At this time, the first power source 25 independently and sufficiently supplies the power to the anion generator 35 so as to generate the anion and to control load of an entire system, and the second power source 45 independently supplies the power to the ozone generator 50, thereby efficiently generating the anion and the ozone. The first and second power source 25, 45 has a transformer and a rectifier so as to receive general supply voltage and then generate a proper voltage for generating the ozone and the anion.

The ozone generator comprises a cylindrical dielectric body 520 which is formed of quartz or glass, an external electrode 540 which is formed of a spring type conductor apart from the dielectric body 520 at a distance, and an internal electrode 550 which is formed of the spring type conductor in the dielectric body 520.

Figure 3:
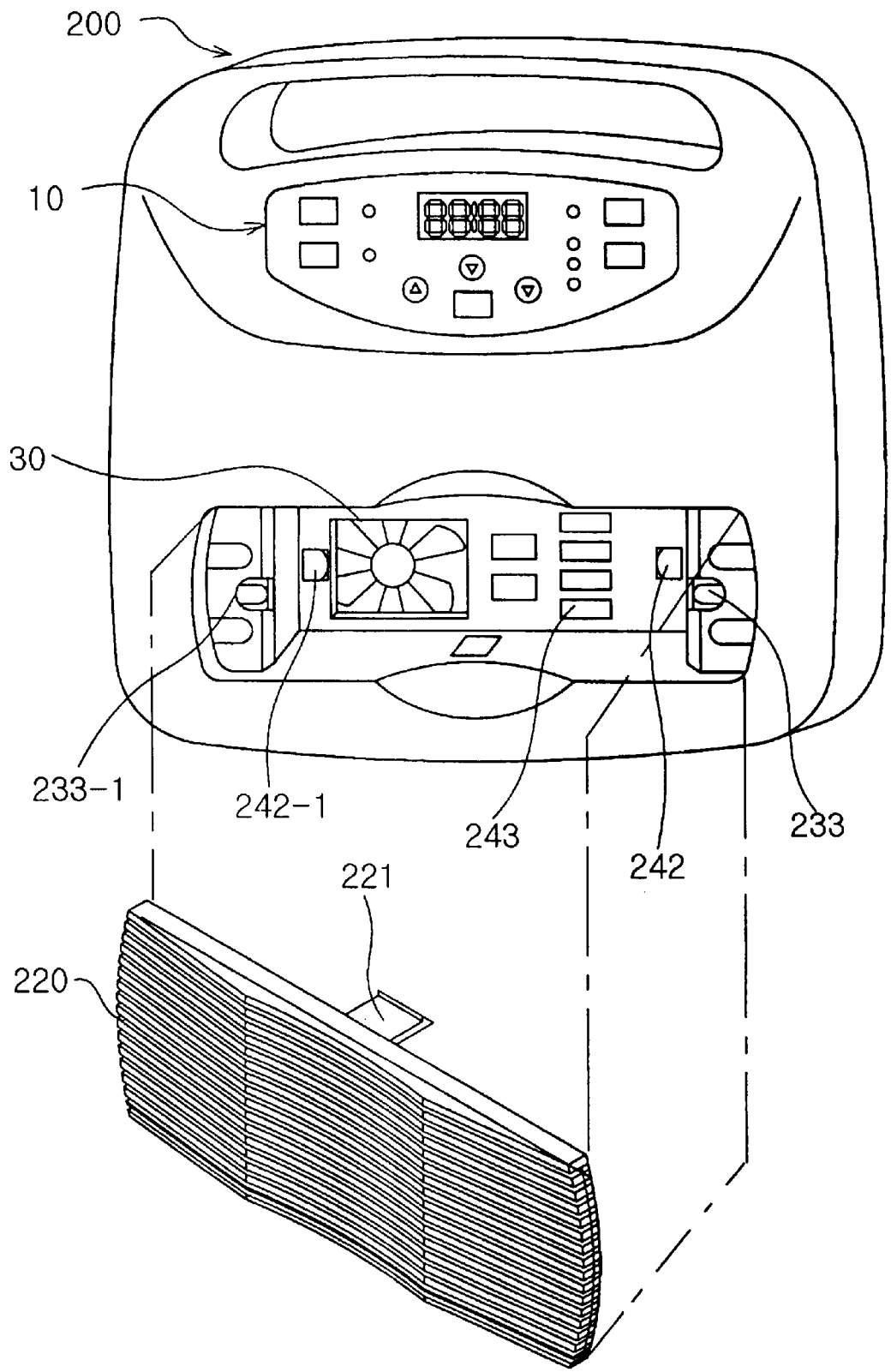
FIG. 3 is a view showing a shape of the apparatus for generating the ozone and anion according to an embodiment of the present invention.
Figure 4:
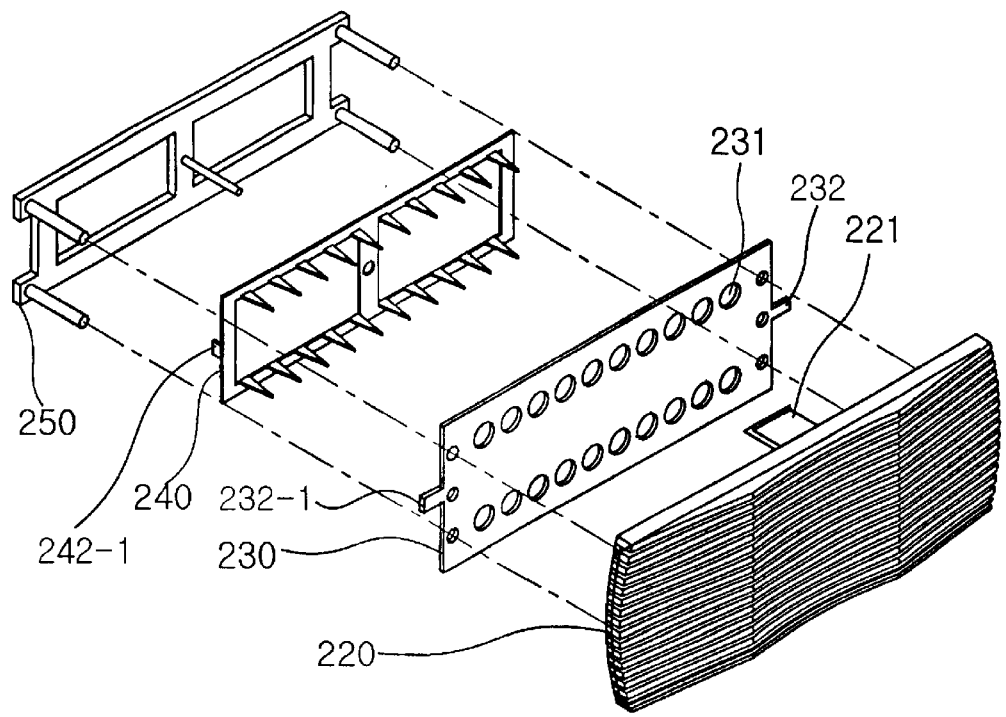
FIG. 4 is an exploded perspective view of an anion generator according to the present invention.
Figure 5:
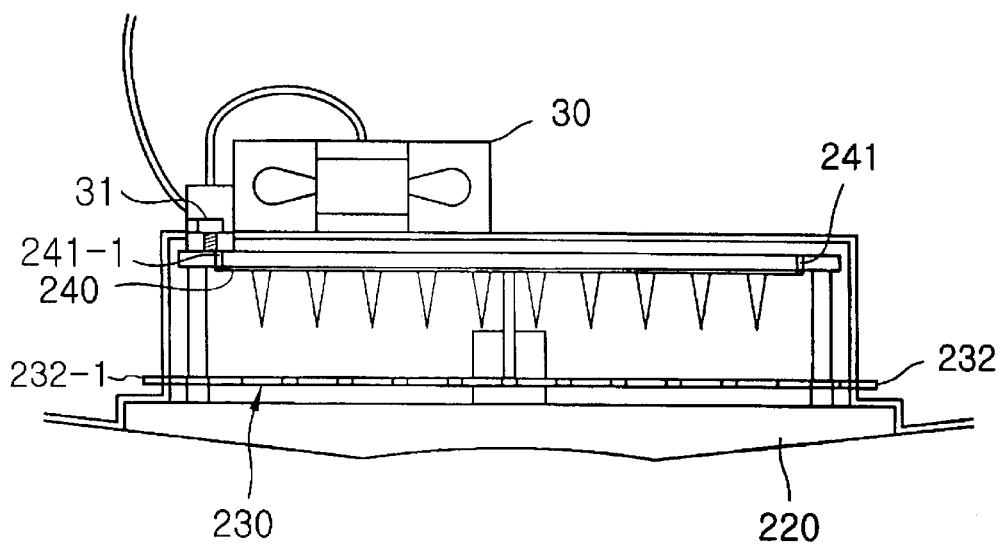
FIG. 5 is a cross-sectional f the FIG. 4.
Figure 6:
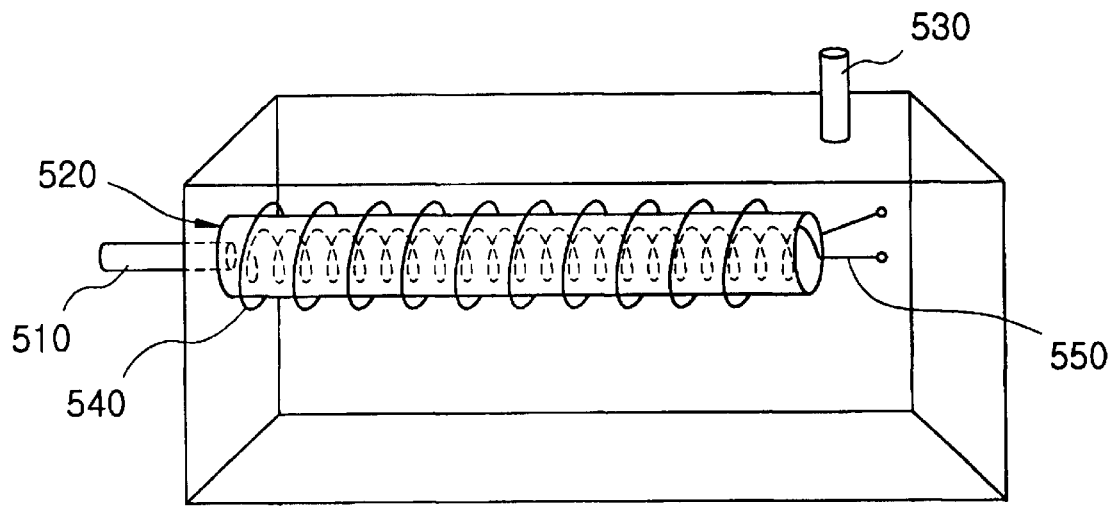
FIG. 6 is a schematic view of an ozone generator of FIG. 2.

As shown in FIGS. 3 to 5, the anion generator 35 is removably disposed at a lower portion of a main body. The anion generator 35 comprises an acicular portion 240 having a plurality of sharp needles at a front face thereof, a fixing frame 250 for fixing the acicular portion 240, a discharging plate 230 having a plurality of discharging holes 231 corresponding to the needles of the acicular portion 240 so as to efficiently generate the anion, and a grill plate 220 for facilely discharging the anion. The acicular portion 240 has a negative terminal 241, 241-1 that is connected with an anion-generating electrode (−). The discharging holes 231 of the discharging plate 230 are disposed to be apart from the acicular portion 240 at a distance.

A positive electrode 232, 232-1 is formed at both sides of the discharging plate 230 to receive positive power. As shown in FIG. 5, at a side of the circulating fan 30, there is formed a safety switch 31 for cutting off the power of the circulating fan 30 when disassembling the anion generator 220.

That is, the positive electrode 232, 232-1 is connected with a positive connecting terminal 233, 233-1, and the negative electrode 241, 241-1 is connected with a negative connecting terminal 242, 242-1 so as to receive the power from the first power source 25 and thus to generate the anion. At this time, when disassembling the anion generator 220, the safety switch 31 stops the circulating fan 30 to prevent an accident. Further, at both sides of the anion generator, there is provided a power-supplying terminal so that the anion generator can be assembled and disassembled without distinction of an upper and lower portion.

Moreover, a PIOS 243 is disposed at an inner main body 200 of the anion generator so as to naturally discharge the anion and various far-infrared rays.

Figure 8:
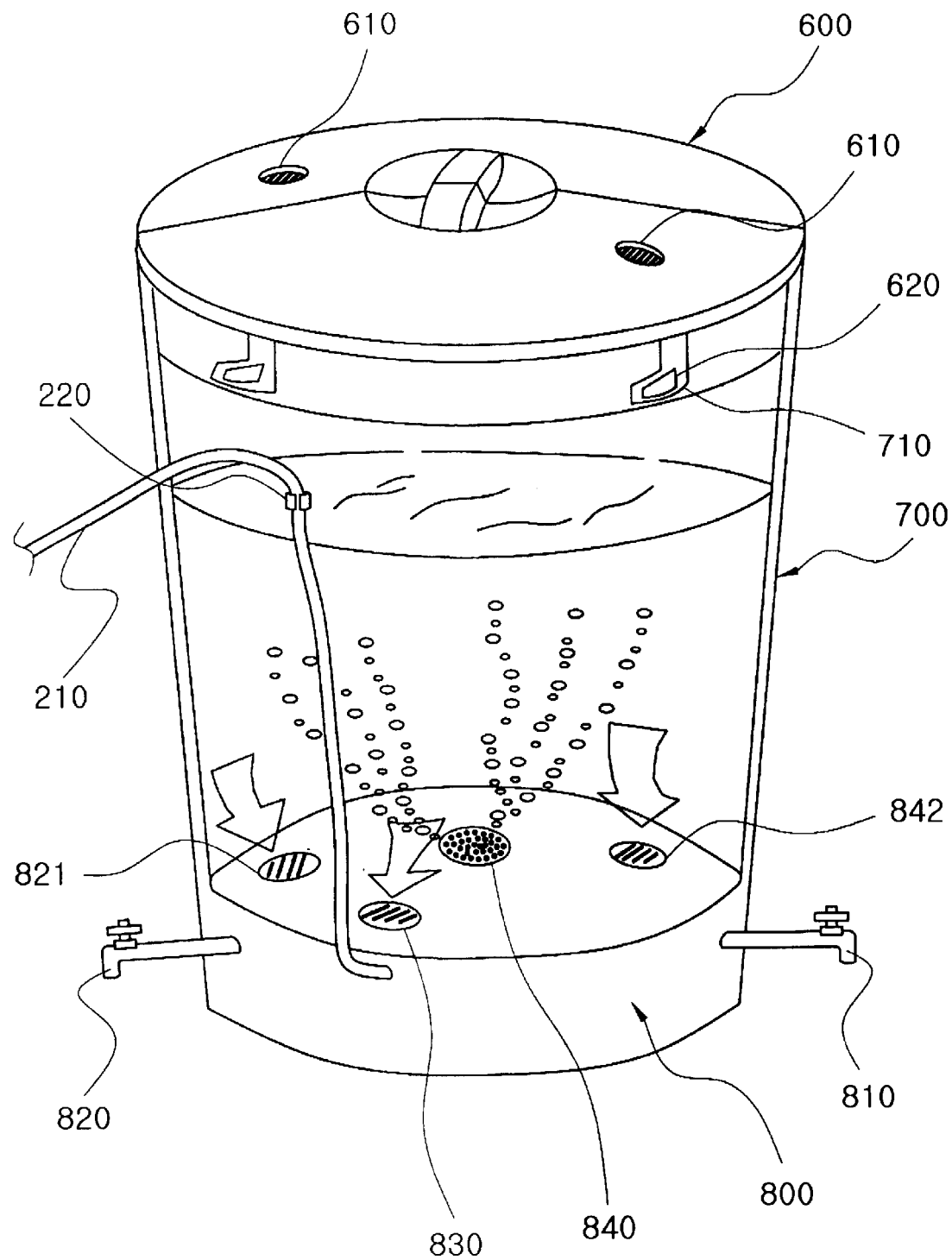
FIG. 8 is a perspective view of the ozone container according to the present invention.
Figure 9:
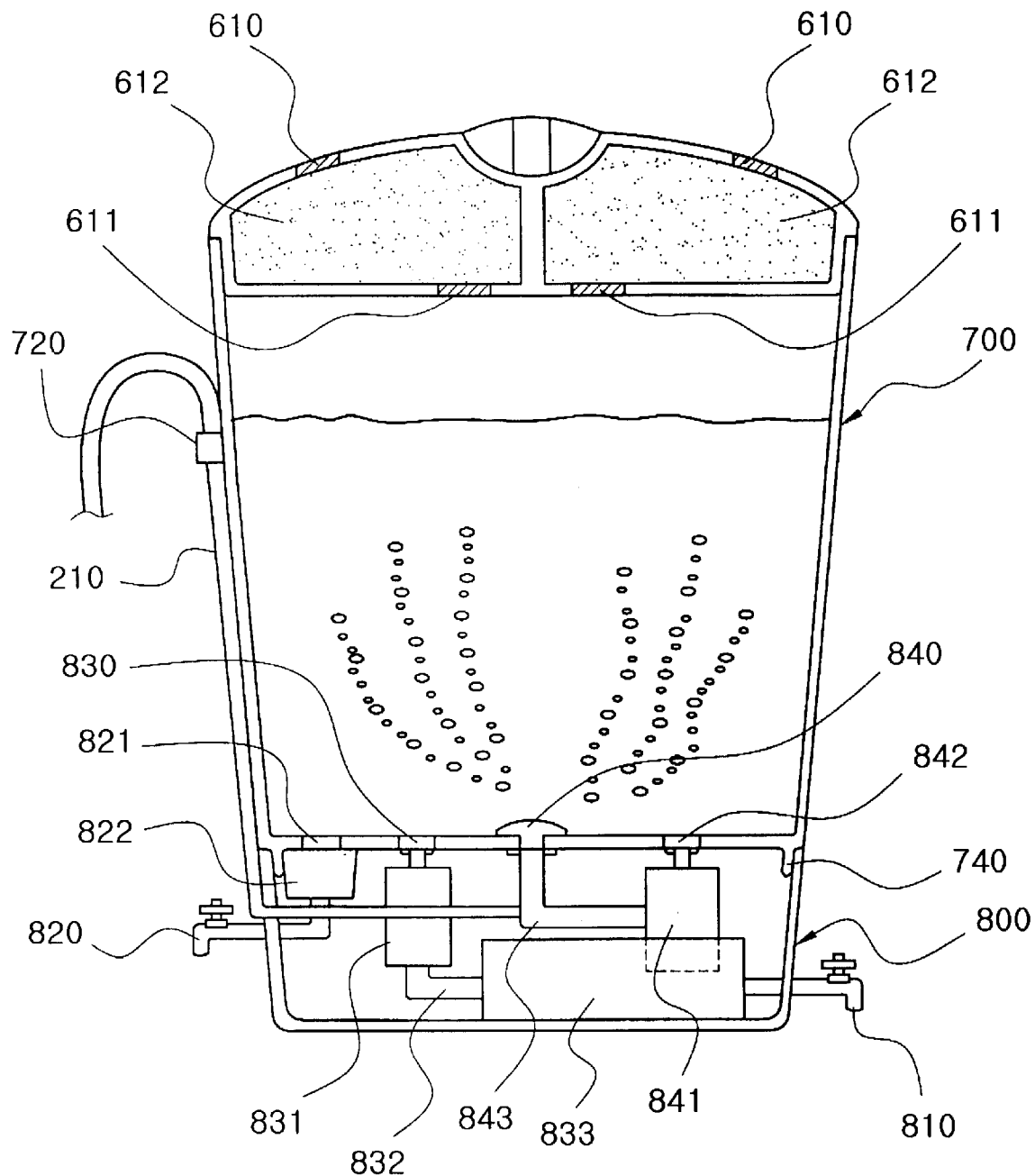
FIG. 9 is a cross-sectional view of the ozone container of FIG. 8.
Figure 10:
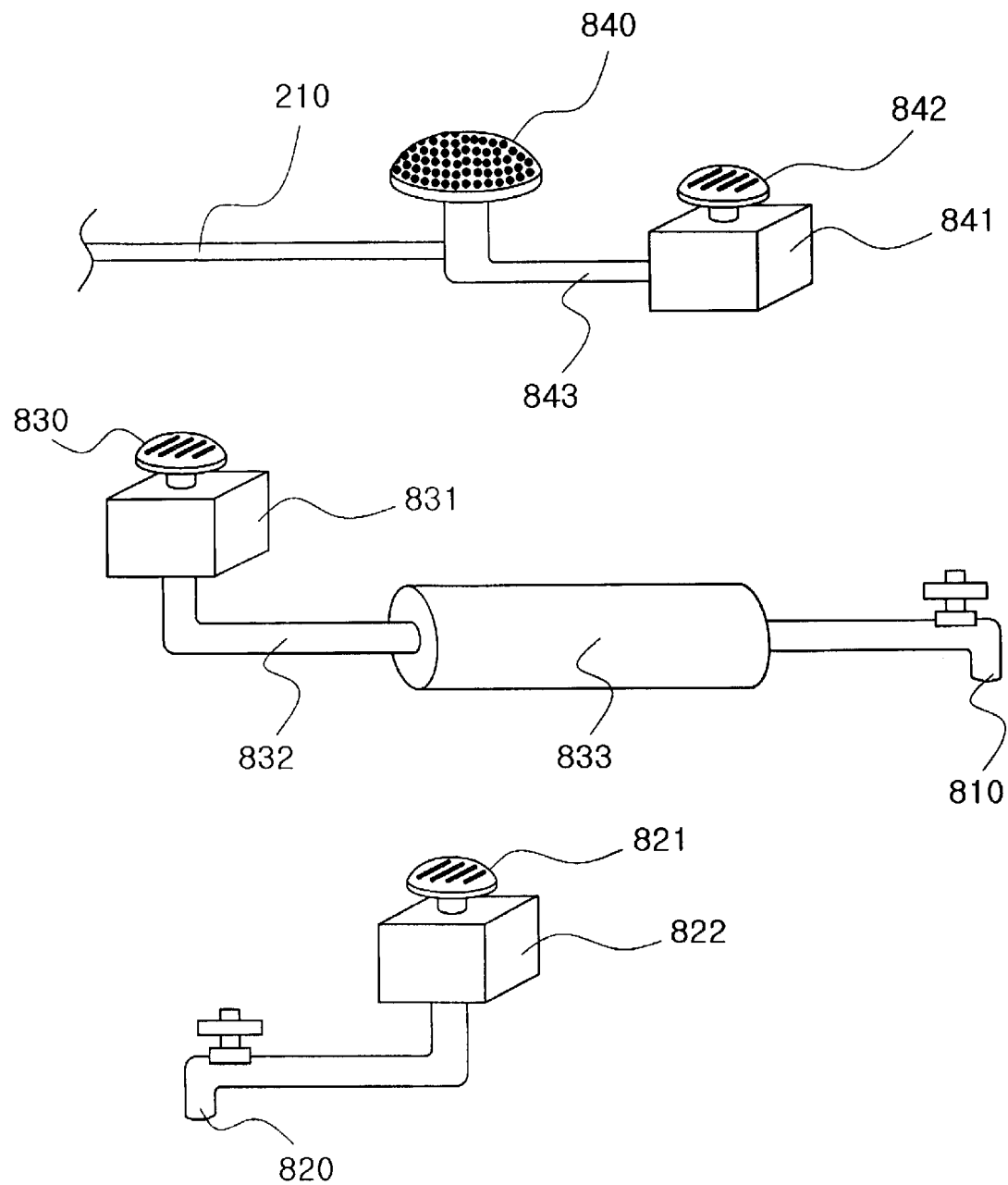
FIG. 10 is a view showing components of the ozone container.

FIG. 8 is an ozone container according to the present invention, FIG. 9 is a cross-sectional view of the ozone container of FIG. 8, and FIG. 10 shows components of the ozone container of FIG. 8.

It is preferable that a typical water purifier is used as the water purifier 100. However, as shown in FIGS. 9 and 10, the ozone container comprises a main body 700 for receiving the ozone supplied through the ozone-supplying hose 210 from an external ozone generator, a cover 600 for removing residual ozone that is reacted with raw water in the main body 700, and a main unit 800 that efficiently supplies the ozone supplied from an outside and includes various devices for purifying the raw water so that a user can drink.

The cover 600 is comprised of activated carbon 612 which is provided at an inner portion thereof to remove the residual ozone, an ozone intake port 611 through which the residual ozone in the ozone container is sucked, an outlet port 610 for discharging the residual ozone to an outside, and a locking pin 620 for sealingly coupling the cover 600 to the main body 700.

Therefore, after the ozone supplied from the outside is reacted with the raw water to sterilize and purify the water, the residual ozone is sucked through the ozone intake port 610 of the cover 600 and filtered through the activated carbon 612 and then discharged through the outlet port 610.

Further, the activated carbon 612 also removes various odors generated when the raw water is reacted with the ozone.

The main body 700 has a locking groove 710 that is engaged with the locking pin 620 of the cover 600 so that the cover 600 is sealingly mounted on the main body 700. The main body 700 also has a fixing guide 740 for guiding the main unit 800 so that the main unit 800 is facilely assembled or disassembled with the main body 700.

A hose-fixing pin 720 for fixing the external ozone-supplying hose 730 is disposed at an upper portion of the main body 700 to fix the ozone-supplying hose 730. Therefore, it is prevent that the raw water in the main body 700 is flowed backward using a property that the ozone is heavier than air.

The main unit 800 is comprised of an underwater motor 841 for maximally dissolve the ozone supplied from the outside in the raw water, a water purifying portion for purifying the raw water sterilized by the ozone so that a user can drink, a wastewater discharging portion for discharging wastewater in which residual agricultural chemicals on vegetables and fruits are resolved. The underwater motor further functions to mix the sucked raw water with the ozone supplied from the outside and then discharge the water.

The main unit 800 further comprises a raw water intake port 842 that is formed at a bottom face of the main body 700 to suck the raw water, and an ozone discharging port 840 for discharging the mixed raw water.

That is, the underwater motor 841 having a desired output efficiently mixes the external ozone with the raw water so that the ozone is equally supplied to the entire raw water. Preferably, the ozone discharging port 840 is radially formed.

The water-purifying portion is comprised of a former processing filter 831 for firstly processing the raw water processed by the ozone, an activated carbon filter 833 for removing various chemical substances and contaminants, and a purified water outlet port 810 for supplying the purified water through the activated carbon filter 833 to the outside. The former processing filler 831 removes the contaminants and the foreign substances of $5\mu$ or more, e.g., rust dregs like iron oxide, earth and sand, hairs, various floating matters formed of solid substances and deposits, etc.

Herein, a membrane filter may be used as the activated carbon filter 833.

Further, the wastewater-discharging portion is to discharge the wastewater in which residual agricultural chemicals on vegetables and fruits are resolved. The wastewater-discharging portion is comprised of a wastewater intake port 821 for receiving the wastewater, a filter 822 for filtering relatively large-sized substances such as various floating substances and deposits, and a wastewater outlet port 820 for discharging the wastewater to the outside.

Preferably, a typical filter is used as the filter 822 so as to prevent clogging of the wastewater outlet port 820 and the wastewater intake port 821.

In the water purifier 100 according to the present invention, as described above, in case of resolving the residual agricultural chemicals on the vegetables and fruits, the water purifier 100 receives the ozone generated from the external ozone generator 200 through the ozone-supplying hose 730. Then, if the vegetables and fruits are provided in the raw water so as to be sufficiently submerged in the water, the supplied ozone is mixed with the raw water sucked through the raw water intake port 842 by the underwater motor 841 and then discharged through the raw outlet port 840 so as to resolve and remove the residual agricultural chemicals on the vegetables and fruits.

Then, the residual ozone is sucked through the intake port 611 of the cover 600 and filtered through the activated carbon 612 in the cover 600 and then discharged through the outlet port 610.

Further, in case the raw water is used as the water for drinking, the raw water is sucked through a water intake port 830 and firstly purified through the former processing filter 831 and then completely purified through the activated carbon filter 833. Then, the purified water is supplied through the purified water outlet port 810 to be facilely supplied to the user as the water for drinking.

The activated carbon is used as an adsorbent and is called "AC". The AC is formed by drying carbonaceous ash, wood, brown coal and peat with an activator by distillation or by activating charcoal with vapor. Particularly, coconut skin AC formed of a coconut skin is widely known. The AC is provided in powder state or particle state, and used for removing of the contaminants in addition to using as a deodorizer and decolorizer.

The wastewater generated when sterilizing the vegetables and the fruits is transferred through the wastewater intake port 821 to the filter 822 so as to be filtered, and then discharged through the wastewater outlet port 820.

Therefore, the ozone can be used for removing the residual agricultural chemicals on the vegetables and fruits as well as purifying the raw water into the water for drinking.

Further, each of the filters is easily separated from the main body 700 to be replaced with new one, thereby providing convenience to the user.

Figure 7:
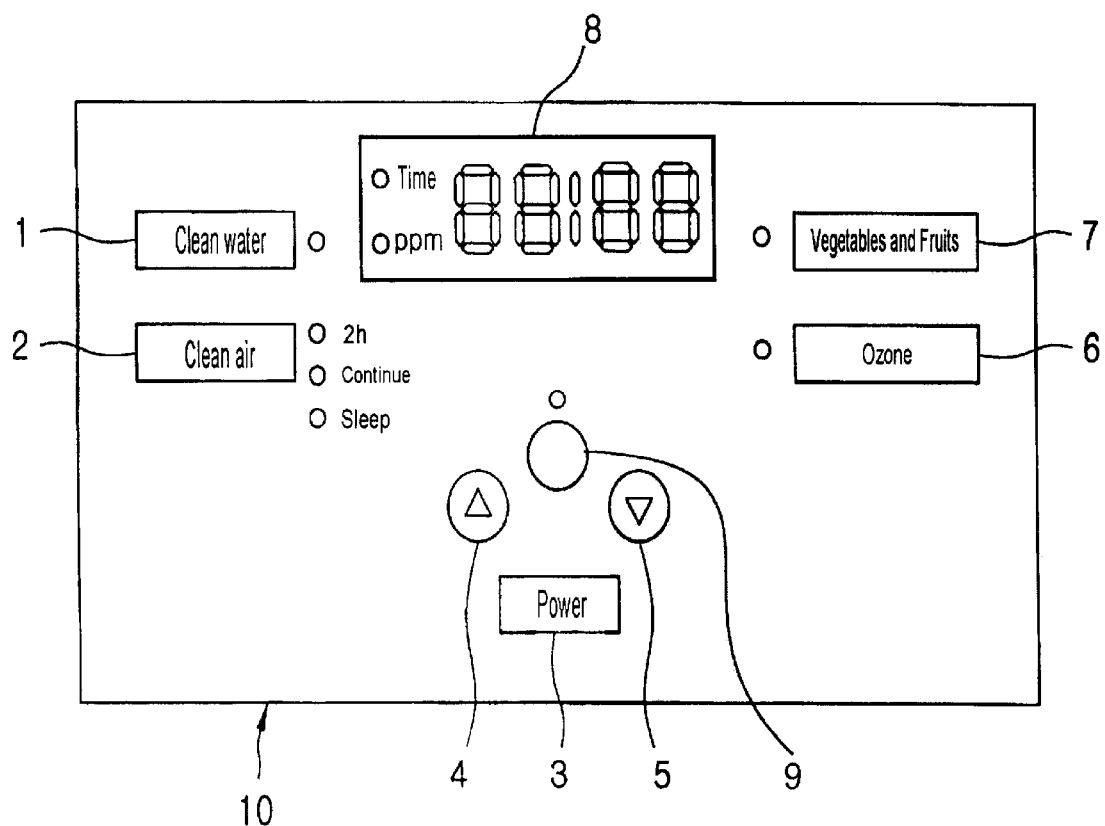
FIG. 7 is a view of an operating portion according to an embodiment of the present invention.

FIG. 7 is a view of an operating portion according to an embodiment of the present invention. Referring to FIG. 7, an operation of the apparatus according to the present invention will be fully described. An operating portion 10 is comprised of a vegetable/fruit button 7, an operating lamp of the vegetable/fruit button 7, an ozone button 6, an operating lamp of the ozone button 6, a clean water button 1, an operating lamp of the clean water button 1, a clean air button 2 for purifying the air, an operating lamp of the clean air button 2, a time and ozone increasing button 4, a time and ozone decreasing button 5, a power button 5, a reserving button 9 and a number displaying window 8.

If one of the vegetable/fruit button 7, the ozone water button 6 or the clean water button 1 is selected, the ozone is generated. The vegetable/fruit button 7 is to completely remove and sterilize the residual agricultural chemicals, synthetic detergents and various germs (bacteria, viruses and molds, etc.) on the vegetables and the fruits so as to maintain freshness when storing the vegetables and the fruits for a long time. Therefore, the vegetable/fruit button 7 is a functioning button suitable for using in sterilizing and cleaning of table services and kitchen utensils. The ozone button 6 is to sterilize the germs and the viruses in the raw water, such as colon bacilli, enteroviruses, vibrios, O-157 and molds, etc. so as to be capable of using the water for washing face and hair, bathing and brushing teeth but not for drinking, thereby obtaining an beauty effect. The clean water button 1 is to generate the anion and the ozone at the same time and thus to remove organic substances and heavy metals in the raw water so as to provide the water for drinking, which is completely harmless in an aseptic state and contains a proper amount of minerals, a very small amount of carbonic acid gas and a sufficient amount of oxygen.

The clean air button 2 generates the anion for sterilizing and purifying the air. If the clean air button 2 is pushed once, the operating lamp of the clean air button 2 shows a green color and an air cleaning operation of the anion generator is performed for a predetermined time. If the clean air button 2 is pushed twice, the operating lamp shows a red color and the operation is continuously performed. If the clean air button 2 is pushed three times, the operating lamp shows an orange color and the operation is performed in a sleep mode. That is, an operation of the circulating fan 30 is stopped so that the anion generator is silently driven. Further, if the clean air button 2 is pushed four times, the anion generator is stopped.

In addition, if the clean air button 2 is pushed, a guiding message stored in the voice-storing portion 65 is output through the speaker 70. That is, if the button is pushed once, the guiding message is "operation for (a desired time)". If the button is pushed twice, the message "continuous operation" is output. If the button is pushed three times, the message "sleep mode operation" is output. If the button is pushed four times, the message "operation is stopped" is output. Moreover, various kinds of messages can be stored in the voice-storing portion 65 so that, if each of the buttons is pushed, a corresponding message is output.

In case of the vegetable/fruit button 7, the ozone button 6 and the clean water button 1, an operating time thereof is predetermined. However, the operating time may be adjusted using the time and ozone increasing and decreasing buttons 4, 5.

Further, the number displaying button 8 displays an amount of generated ozone in ppm unit. That is, in case the number displaying button 8 displays the time, the time and ozone increasing and decreasing buttons 4, 5 control the time. In case the number displaying button 8 displays the amount of ozone in the ppm unit, the time and ozone increasing and decreasing buttons 4, 5 control the amount of ozone.

When the ozone-generating buttons and the clean air button 2 are operated at the same time to perform the sterilizing operation and the purifying operation, the operating lamp of the clean air button 2 is switched on and off, so that the user can easily recognize the operation state.

Further, if the vegetable/fruit button 7 is pushed, the ozone is generated for the predetermined time, and then the anion is generated for a desired time to purify the sterilizing power.

The power button 3 controls the poser source supplied to the ozone and anion generator. Whenever all of the buttons are operated, bell sound is generated so that the user can easily recognize the operation. Also, when the operation is completed, the bell sound is generated.

And, all of the buttons except the power button 3 can be used with reserving button 9 so that all functions of the buttons can be reserved. That is, after the reserving button 9 is selected, the operating lamp of the reserving button 9 is switched on. And then each functioning button is selected. Sequentially, the time and ozone increasing and decreasing buttons 4, 5 are selected to set a reserving time. Then, the reserving button 9 is pushed to complete the reserving operation. At this time, the lamp is continuously switched on and off during the reserving operation so that the user can recognize the operation.

According to the apparatus for generating the ozone and the anion according to the present invention, the ozone and the anion can be individually or simultaneously generated.

Further, according to the present invention, the purifying function of the water and the sterilizing function of the vegetable/fruit by the ozone is performed using a separate power-supplying unit, thereby improving performance thereof. The water purifier and the ozone container are separately used, thereby providing convenience to the user. A separate safety switch is provided to prevent an accident when disassembling the anion generator.

While the present invention has been described in detail, it should be understood that various changes, substitutions and alterations could be made hereto without departing from the spirit and scope of the invention as defined by the appended claims.

What is claimed is:

1. An apparatus for generating ozone and anion to clean air and sterilize water for drinking and various vegetables/fruits, comprising:
    an ozone generator for generating ozone having a desired concentration;
    an ozone generator-driving portion for driving the ozone generator;
    a second power source for supplying power to the ozone generator-driving portion;
    an anion generator for generating anion having a desired quantity of electric charge;
    an anion generator-driving portion for driving the anion generator;
    a circulating fan for facilely circulating the anion generated from the anion generator to outside of said apparatus;
    a first power source for supplying power to the anion generator-driving portion;
    a selecting valve for selectively discharging the anion generated from the anion generator to a water purifier or an ozone container;
    an activated carbon filter for removing specific smell of the ozone introduce through the selecting valve into the water purifier;
    a controlling portion for controlling the entire portions including the anion generator-driving portion and the ozone generator-driving portion;
    an operating portion for inputting an external instruction to the controlling portion; and
    a timer for controlling a reserving function of the operating portion.

2. The apparatus of claim 1, wherein the ozone generator comprises:
    a cylindrical dielectric body which is formed of quartz or glass;
    an external electrode which is formed of a spring conductor apart from the dielectric body at a distance; and
    an internal electrode which is formed of the spring conductor in the dielectric body.

3. The apparatus of claim 1, wherein the anion generator comprises:
    an acicular portion having a plurality of sharp needles at a front face thereof;
    a fixing frame for fixing the acicular portion;
    a discharging plate having a plurality of discharging holes corresponding to the needles of the acicular portion so as to efficiently generate the anion; and
    a grill plate for facilely discharging the anion,
    wherein the acicular portion has a negative terminal, that is connected with an anion-generating electrode (−), and the discharging holes of the discharging plate are disposed to be apart from the acicular portion at a distance, and a power-supplying terminal is provided at both sides of the anion generator so that the anion generator can be assembled and disassembled without distinction of an upper and lower portion.

4. The apparatus of claim 1, wherein the operating portion comprises:
    a vegetable/fruit button which is provided to completely remove and sterilize residual agricultural chemicals, synthetic detergents and various germs on the vegetables and the fruits so as to maintain freshness when storing the vegetables and the fruits for a long time, and to sterilize and clean table services and kitchen utensils;
    an ozone button which is provided to obtain a beauty effect but not used as water for drinking;
    a clean water button which is provided to provide the water for drinking, which is completely harmless in an aseptic state;
    a clean air button that generates the anion for sterilizing and purifying the air, and is performed for a predetermined time, or continuously performed, or performed in a sleep mode;
    a number displaying button that is operated or controlled by the time and ozone increasing and decreasing buttons, when displaying a time and when displaying the amount of ozone in the ppm unit; and
    a reserving button that automatically generates the anion after completing a function of the vegetable/fruit button, the ozone button and the clean water button, and that is interlocked with the timer so as to reserve each function of the buttons.

5. The apparatus of claim 1, further comprising:
    an voice storing portion for informing an operation of the operating portion and whether each portion is operated, with a voice; and
    a speaker for outputting the voice of the voice storing portion.

6. The apparatus of claim 1, wherein the ozone container comprises:
    a main body for receiving the ozone supplied through the ozone-supplying hose from an external ozone generator;
    a cover for removing residual ozone that is reacted with raw water in the main body; and
    a main unit that efficiently supplies the ozone supplied from an outside and includes various devices for purifying the raw water so that a user can drink.

7. The apparatus of claim 6, the cover comprises:
    an ozone intake port through which the residual ozone in the ozone container is sucked;
    an activated carbon which is provided to remove the residual ozone;
    an outlet port for discharging the residual ozone to an outside; and
    a locking pin for sealingly coupling the cover to the main body.

8. The apparatus of claim 6, wherein the main unit comprises:
    a raw water intake for sucking raw water from the main body;
    an underwater motor for mixing the ozone supplied from an outside with the sucked raw water and then discharging the mixed raw water;

an ozone discharging port for discharging the mixed raw water;

a former processing filter for firstly processing the raw water processed by the ozone so as to remove contaminants, foreign substances, floating matters formed of solid substances and deposits of 5 μm or more:

an activated carbon filter for removing various chemical substances and contaminants;

a purified water outlet port for supplying the purified water through the activated filter to the outside;

a wastewater intake port for receiving the wastewater;

a filter for filtering relatively large-sized substances such as various floating substances and deposits; and a wastewater outlet port for discharging the wastewater to the outside.

* * * * *